United States Patent
Zhao et al.

(10) Patent No.: US 11,679,280 B2
(45) Date of Patent: Jun. 20, 2023

(54) MICROWAVE POWER CONTROL DEVICE AND METHOD, AND RADIOTHERAPY EQUIPMENT

(71) Applicants: OUR UNITED CORPORATION, Xi'an (CN); SHENZHEN OUR NEW MEDICAL TECHNOLOGIES DEVELOPMENT CO., LTD., Shenzhen (CN)

(72) Inventors: Hongbin Zhao, Xi'an (CN); Ming Zhong, Xi'an (CN); Huiliang Wang, Xi'an (CN); Haifeng Liu, Xi'an (CN)

(73) Assignees: OUR UNITED CORPORATION, Xi'an (CN); SHENZHEN OUR NEW MEDICAL TECHNOLOGIES DEVELOPMENT CO., LTD., Shenzhen (CN)

( * ) Notice: Subject to any disclaimer, the term of this patent is extended or adjusted under 35 U.S.C. 154(b) by 323 days.

(21) Appl. No.: 17/044,735

(22) PCT Filed: Mar. 26, 2019

(86) PCT No.: PCT/CN2019/079617
§ 371 (c)(1),
(2) Date: Oct. 1, 2020

(87) PCT Pub. No.: WO2019/192347
PCT Pub. Date: Oct. 10, 2019

(65) Prior Publication Data
US 2021/0023397 A1 Jan. 28, 2021

(30) Foreign Application Priority Data

Apr. 4, 2018 (CN) .......................... 201810293921.X

(51) Int. Cl.
*A61N 5/10* (2006.01)

(52) U.S. Cl.
CPC ......... *A61N 5/1081* (2013.01); *A61N 5/1048* (2013.01)

(58) Field of Classification Search
CPC .... A61N 5/10–1084; A61N 2005/1085–1098; A61N 5/02–045
See application file for complete search history.

(56) References Cited

U.S. PATENT DOCUMENTS

| 5,321,271 | A | | 6/1994 | Schonberg et al. |
| 5,855,582 | A | * | 1/1999 | Gildenberg ............ A61B 90/14 600/417 |

(Continued)

FOREIGN PATENT DOCUMENTS

| CN | 1041698 A | 5/1990 |
| CN | 1089178 A | 7/1994 |

(Continued)

OTHER PUBLICATIONS

International Search Report and Written Opinion of corresponding PCT Application PCT/CN2019/079617—17 pages (dated Jun. 17, 2019).

*Primary Examiner* — Thaddeus B Cox
(74) *Attorney, Agent, or Firm* — Knobbe, Martens, Olson & Bear, LLP

(57) ABSTRACT

A microwave power control device can include: a microwave signal generator and a signal distribution circuitry connected to the microwave signal generator. The microwave signal generator is configured to generate microwave signals and transmit the microwave signals to the signal distribution circuitry; and the signal distribution circuitry is configured to distribute the microwave signals to n accelerating tubes according to a target microwave power distribution ratio, n being an integer greater than or equal to 2.

14 Claims, 6 Drawing Sheets

(56) References Cited

U.S. PATENT DOCUMENTS

| | | | |
|---|---|---|---|
| 7,902,530 B1 * | 3/2011 | Sahadevan | A61N 5/1042 250/341.7 |
| 2014/0275708 A1 * | 9/2014 | Leek | A61N 5/1077 600/1 |
| 2015/0085989 A1 * | 3/2015 | Kang | A61N 5/1077 378/138 |

FOREIGN PATENT DOCUMENTS

| | | | | |
|---|---|---|---|---|
| CN | 102526891 A | 7/2012 | | |
| CN | 108392741 A | 8/2018 | | |
| WO | WO-2012025261 A1 * | 3/2012 | | A61N 5/1042 |

\* cited by examiner

MICROWAVE POWER CONTROL DEVICE AND METHOD, AND RADIOTHERAPY EQUIPMENT

The present disclosure is a national phase application of PCT International Application No. PCT/CN2019/079617, filed on Mar. 26, 2019, which claims priority to Chinese Patent Application No. 201810293921.X, filed on Apr. 4, 2018 and entitled "MICROWAVE POWER CONTROL DEVICE AND METHOD, AND RADIOTHERAPY EQUIPMENT", the contents of which are incorporated herein by reference in their entireties.

TECHNICAL FIELD

The present disclosure relates to the field of medical technologies, and in particular relates to a microwave power control device and method, and radiotherapy equipment.

BACKGROUND

In modern medicine, radiotherapies, which adopt high-energy radiation to kill tumor cells, are an important means to treat malignant tumors.

At present, the radiotherapy mainly adopts radiotherapy equipment which includes a radiation treatment head and a microwave power control device. The radiation treatment head, which includes an accelerating tube, is arranged on a rotating gantry and can rotate along with the rotation of the rotating gantry. The microwave power control device is configured to output microwave signals to the accelerating tube in the radiation treatment head to drive the accelerating tube.

SUMMARY

The present disclosure provides a microwave power control device and method, and radiotherapy equipment. The technical solutions of the present disclosure are as follows.

In a first aspect, a microwave power control device is provided, the device includes: a microwave signal generation module and a distribution module connected to the microwave signal generation module, wherein the microwave signal generation module is configured to generate microwave signals and transmit the microwave signals to the distribution module; and the distribution module is configured to distribute the microwave signals to n accelerating tubes according to a target microwave power distribution ratio, n being an integer greater than or equal to 2.

Optionally, the distribution module comprises: a microwave transmission sub-module and n power regulation sub-modules, wherein the microwave transmission sub-module is connected to the microwave signal generation module, and is configured to respectively transmit the microwave signals generated by the microwave signal generation module to the n power regulation sub-modules; and the n power regulation sub-modules are configured to distribute the microwave signals to the n accelerating tubes according to the target microwave power distribution ratio.

Optionally, wherein the power regulation sub-module is an adjustable power switch comprising: a coupler, a first adjustable phase shifter, and a second adjustable phase shifter, wherein a first end of the coupler is connected to the microwave transmission sub-module, a second end of the coupler is connected to a first short-circuit waveguide via the first adjustable phase shifter, a third end of the coupler is connected to a second short-circuit waveguide via the second adjustable phase shifter, and a fourth end of the coupler is connected to a corresponding accelerating tube.

Optionally, the microwave transmission sub-module is a circulator with m ports, m being an integer greater than or equal to n+1; and wherein a $1^{st}$ port of the circulator is connected to the microwave signal generation module, and a $2^{nd}$ port to a $(n+1)^{th}$ port of the circulator are respectively connected to the n power regulation sub-modules.

Optionally, n is 2, m is 4, and a $4^{th}$ port of the circulator is connected to a microwave load.

Optionally, the microwave signal generation module comprises a solid-state modulator and a magnetron.

In a second aspect, a radiotherapy equipment is provided, the radiotherapy equipment includes: n accelerating tube carriers and the microwave power control device according to any one of the first aspects, wherein an accelerating tube in each of the accelerating tube carriers is connected to a distribution module of the microwave power control device.

Optionally, the accelerating tube carrier includes: at least one of an X-ray treatment head and an X-ray diagnostic head.

Optionally, when n is 2, the X-ray treatment head includes an X-ray conformal intensity modulation treatment head and an X-knife treatment head.

Optionally, the radiotherapy equipment further includes a gantry, wherein the n accelerating tube carriers and the microwave power control device are arranged on the gantry.

In a third aspect, a microwave power control method is provided and is applicable to the microwave power control device according to any one of the first aspects. The method includes:

generating microwave signals by a microwave signal generation module;

transmitting, by the microwave signal generation module, the microwave signals to a distribution module; and distributing, by the distribution module, the microwave signals to n accelerating tubes according to a target microwave power distribution ratio, n being an integer greater than or equal to 2.

Optionally, the distribution module includes: a microwave transmission sub-module and n power regulation sub-modules, wherein distributing, by the distribution module, the microwave signals to the n accelerating tubes according to the target microwave power distribution ratio includes:

transmitting, by the microwave transmission sub-module, the microwave signals to the n power regulation sub-modules respectively, and distributing, by the n power regulation sub-modules, the microwave signals to the n accelerating tubes according to the target microwave power distribution ratio.

In a fourth aspect, a microwave power control method is provided and is applicable to the radiotherapy equipment according to any one of the second aspects. The method includes:

controlling a microwave signal generation module to generate microwave signals;

controlling the microwave signal generation module to transmit the microwave signals to a distribution module; and controlling the distribution module to distribute the microwave signals to n accelerating tubes according to a target microwave power distribution ratio, n being an integer greater than or equal to 2.

Optionally, the distribution module includes: a microwave transmission sub-module and n power regulation sub-modules, wherein controlling the distribution module to distribute the microwave signals to the n accelerating tubes according to the target microwave power distribution ratio includes:

controlling the microwave transmission sub-module to transmit the microwave signals to the n power regulation sub-modules respectively, and controlling the n power regulation sub-modules to distribute the microwave signals to the n accelerating tubes according to the target microwave power distribution ratio.

In a fifth aspect, a microwave power control device is provided. The device includes: a memory and a processor, wherein a computer program is stored in the memory; and the processor, when calling and executing the computer program stored in the memory, performs the microwave power control method according to any one of the third aspects.

In a sixth aspect, a microwave power control device is provided. The device includes: a memory and a processor, wherein a computer program is stored in the memory; and the processor, when calling and executing the computer program stored in the memory, performs the microwave power control method according to any one of the fourth aspects.

In a seventh aspect, a computer-readable storage medium storing instructions thereon is provided. The instruction, when executed by a processing component, perform the microwave power control method according to any one of the third aspects.

In an eighth aspect, a computer-readable storage medium storing instructions thereon is provided. The instructions, when executed by a processing component, perform the microwave power control method according to any one of the fourth aspects.

BRIEF DESCRIPTION OF DRAWINGS

In order to describe the technical solutions in the embodiments of the present disclosure more clearly, the following briefly introduces the accompanying drawings required for describing the embodiments. Apparently, the accompanying drawings as described below show merely some embodiments of the present disclosure, and persons of ordinary skilled in the art may also derive other drawings from these accompanying drawings without creative efforts.

DESCRIPTION OF EMBODIMENTS

For clearer descriptions of the objects, technical solutions, and advantages of the present disclosure, the embodiments of the present disclosure are further described in detail in combination with the accompanying drawings.

In the current radiation therapy equipment, microwave power control devices and accelerating tubes are arranged in a one-to-one correspondence, and each microwave power control device can only drive one accelerating tube. Thus, the function of the microwave power control device is relatively limited, and the cost of the radiotherapy equipment is relatively high.

Figure 1:
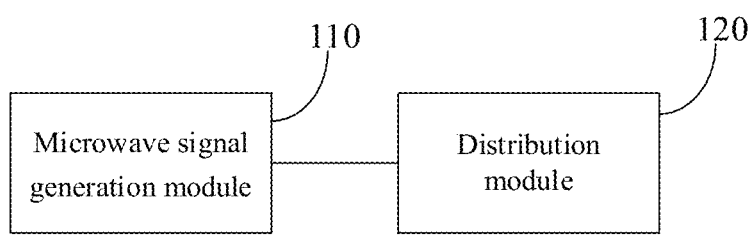
FIG. 1 is a schematic structural diagram of a microwave power control device according to an embodiment of the present disclosure.

FIG. 1 is a schematic structural diagram of a microwave power control device according to an embodiment of the present disclosure. As shown in FIG. 1, the microwave power control device includes: a microwave signal generation module 110, and a distribution module 120 connected to the microwave signal generation module 110.

The microwave signal generation module 110 is configured to generate microwave signals and transmit the microwave signals to the distribution module 120.

The distribution module 120 is configured to distribute the microwave signals to n accelerating tubes according to a target microwave power distribution ratio, wherein n is an integer greater than or equal to 2.

Figure 2:
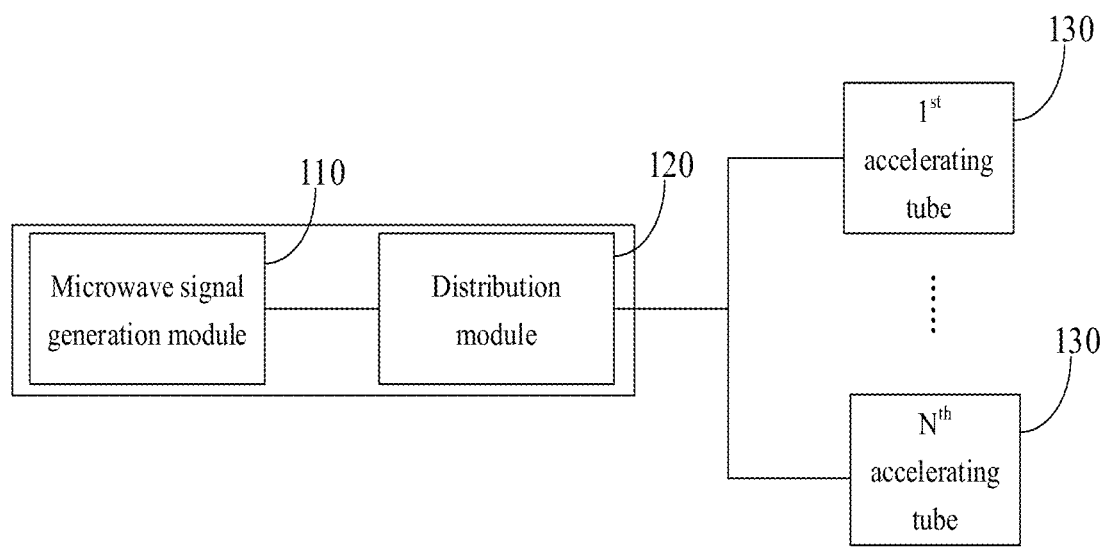
FIG. 2 is a schematic diagram showing an application scenario of a microwave power control device according to an embodiment of the present disclosure.

Optionally, FIG. 2 is a schematic diagram showing an application scenario of a microwave power control device according to an embodiment of the present disclosure. As shown in FIG. 2, the microwave power control device shown in FIG. 1 is configured to distribute the microwave signals to n accelerating tubes 130 according to the target microwave power distribution ratio.

In summary, the microwave power control device provided by the embodiment of the present disclosure includes the microwave signal generation module and the distribution module, wherein the microwave signal generation module generates the microwave signals and transmits the microwave signals to the distribution module, and the distribution module distributes the microwave signals to at least two accelerating tubes according to the target microwave power distribution ratio. Compared with related arts, as one microwave power control device can drive at least two accelerating tubes at a time, the microwave power control device is richer in function, and the cost of the radiotherapy equipment can be reduced.

In the embodiment of the present disclosure, the microwave power control device can distribute the microwave signals to the n accelerating tubes according to the target microwave power distribution ratio, and can drive a plurality of accelerating tubes at a time. The target microwave power distribution ratio may be preset or determined in real time, and may be a fixed or variable value, which is not limited in the embodiments of the present disclosure. The target microwave power distribution ratio may be any microwave power distribution ratio. That is, the microwave power control device may distribute power among the plurality of the accelerating tubes according to any microwave power distribution ratio.

Optionally, the target microwave power distribution ratio may be set according to actual requirements. For example, if three accelerating tubes are provided, and the target microwave power distribution ratio is 1:2:3, then the microwave power control device may distribute the microwave signal of 1/6 power to the $1^{st}$ accelerating tube, the microwave signal of 1/3 power to the $2^{nd}$ accelerating tube, and the microwave signal of 1/2 power to the $3^{rd}$ accelerating tube. Of course, the microwave power control device can distribute the microwave signal of full power to any one accelerating tube, and does not distribute any microwave signal to the remaining accelerating tubes, which is not limited in the embodiments of the present disclosure.

Figure 3:
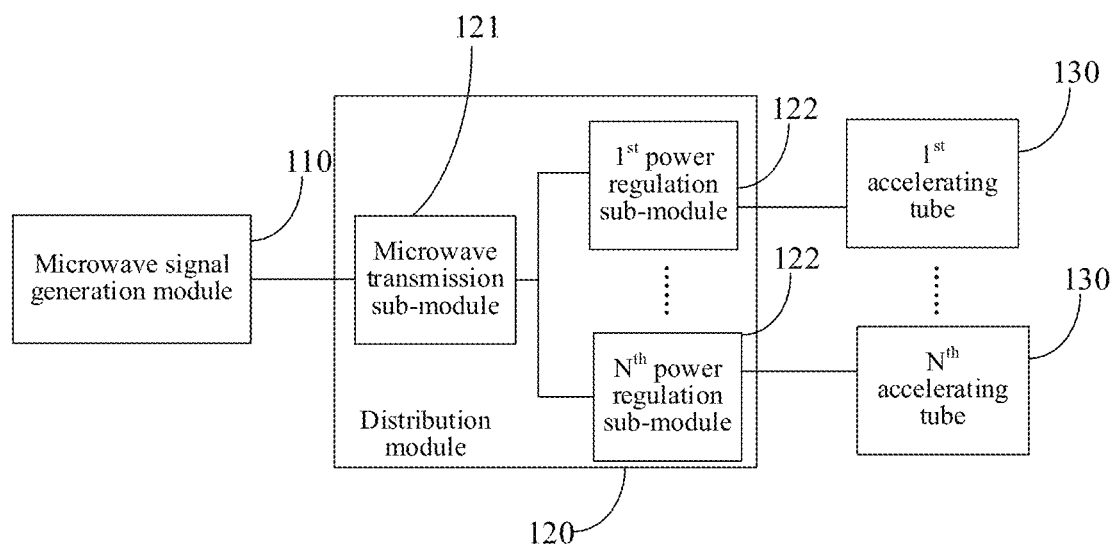
FIG. 3 is a schematic diagram of an application scenario showing another microwave power control device according to an embodiment of the present disclosure.

FIG. 3 is a schematic diagram showing an application scenario of another microwave power control device according to an embodiment of the present disclosure. As shown in FIG. 3, the microwave power control device may include: a microwave signal generation module 110, and a distribution module 120 connected to the microwave signal generation module 110.

The microwave signal generation module 110 is configured to generate microwave signals and transmit the microwave signals to the distribution module 120.

The distribution module 120 is configured to distribute the microwave signals to n accelerating tubes 130 according to a target microwave power distribution ratio, wherein n is an integer greater than or equal to 2.

The distribution module 120 may include: a microwave transmission sub-module 121 and n power regulation sub-modules 122.

The microwave transmission sub-module 121 may be connected to the microwave signal generation module 110, and is configured to transmit the microwave signals generated by the microwave signal generation module 110 to the n power regulation sub-modules 122, respectively. The n power regulation sub-modules 122 are configured to distribute the microwave signals to the n accelerating tubes 130 according to the target microwave power distribution ratio.

In example embodiments, the microwave signal generation module may include a solid-state modulator and a magnetron. The magnetron is configured to generate microwave signals, and the solid-state modulator is configured to modulate the microwave signals generated by the magnetron and output the modulated microwave signals.

Optionally, the power regulation sub-module may be an adjustable power switch. In example embodiments, the adjustable power switch may be an adjustable ferrite power switch.

Figure 4:
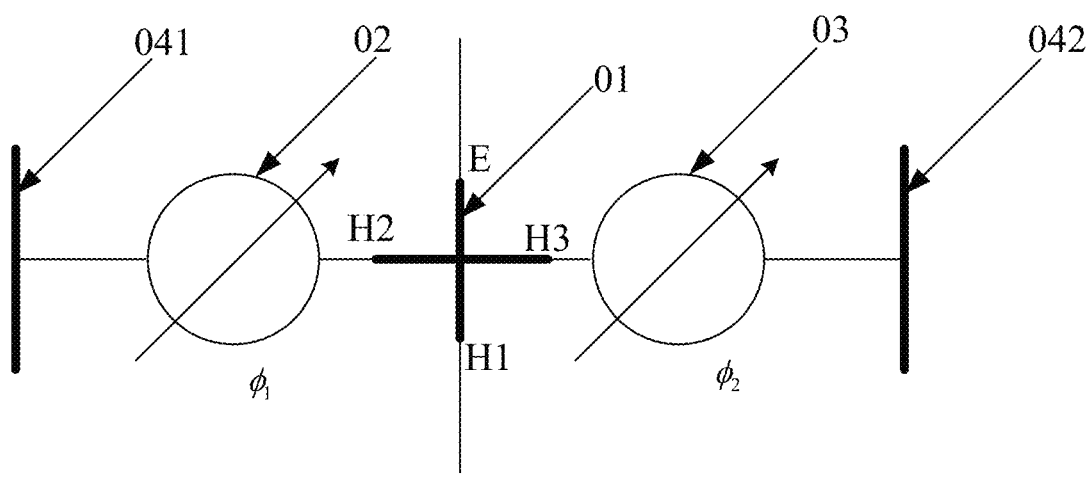
FIG. 4 is a schematic diagram of an adjustable power switch according to an embodiment of the present disclosure.

In example embodiments, FIG. 4 is a schematic diagram of an adjustable power switch according to an embodiment of the present disclosure. As shown in FIG. 4, the adjustable power switch may include: a coupler 01, a first adjustable phase shifter 02, and a second adjustable phase shifter 03.

The first end H1 of the coupler 01 is configured to be connected to the microwave transmission sub-module. The second end H2 of the coupler 01 is connected to a first short-circuit waveguide 041 via the first adjustable phase shifter 02. The third end H3 of the coupler 01 is connected to a second short-circuit waveguide 042 via the second adjustable phase shifter 03. The fourth end E of the coupler 01 is connected to the accelerating tube. In example embodiments, the coupler may be a 3 dB hybrid coupler.

The first adjustable phase shifter 02 and the second adjustable phase shifter 03 are configured to adjust the phase of the microwave signal passing therethrough, so that the microwave signals input to the microwave transmission sub-module can be distributed to the n accelerating tubes according to the target microwave power distribution ratio, and the microwave signal of residual power is output to the microwave transmission sub-module via the first end H1 of the coupler under the reflection of the corresponding short-circuit waveguide.

In example embodiments, the n accelerating tubes include two accelerating tubes, namely, a first accelerating tube and a second accelerating tube; and the n power regulation sub-modules include two power regulation sub-modules, namely, a first power regulation sub-module and a second power regulation sub-module. For example, the first and second adjustable phase shifters of the first power regulation sub-module are configured to adjust the phase of the microwave signal passing therethrough, so that the microwave signal input to the microwave transmission sub-module is distributed to the first accelerating tube according to the target microwave power ratio, and the microwave signal of residual power is output to the microwave transmission sub-module via the first end of the coupler under the reflection of the corresponding short-circuit waveguide. The first and second adjustable phase shifters of the second power regulation sub-module are configured to adjust the phase of the microwave signal passing therethrough, so that the microwave signal input to the microwave transmission sub-module is distributed to the second accelerating tube according to the target microwave power ratio, and the microwave signal of residual power is output to the microwave transmission sub-module via the first end of the coupler under the reflection of the corresponding short-circuit waveguide.

The adjustable power switch shown in FIG. 4 is taken as an example to illustrate a phase adjustment process of the microwave signal. As shown in FIG. 4, it is assumed that the phase of the microwave signal which is input from the microwave transmission sub-module to the first end H1 of the coupler 01 and passes through the first adjustable phase shifter 02 is $\phi_1$, and the phase of the microwave signal which is input from the microwave transmission sub-module to the first end H1 of the coupler 01 and passes through the second adjustable phase shifter 03 is $\phi_2$, a transmission function corresponding to the first end H1 (the identifier representing the port of the first end H1 is 1) to the fourth end E (the identifier representing the port of the fourth end E is 2) of the coupler 01 can be expressed as:

$$S_{21}(\phi_1,\phi_2)=\tfrac{1}{2}(e^{-j\phi_1}+e^{-j\phi_1})$$

It can be seen from the above formula that when $\phi_1=-\phi_2$, the signal power, namely the amplitude of the transmission function $S_{21}(\phi_1, \phi_2)$, of the microwave signal transmitted from the first end H1 to the fourth end E of the coupler can be expressed as:

$$A = |S_{21}(\phi_1, \phi_2)| = \sqrt{\frac{1 + \cos(2\phi_1)}{2}}.$$

Thus, when $\phi_1=-\phi_2$, that is, when the phase of the microwave signal passing through the first adjustable phase shifter 02 is opposite to the phase of the microwave signal passing through the second adjustable phase shifter 03, the amplitude of the transmission function $S_{21}(\phi_1, \phi_2)$ can be changed by changing $\phi_1$, so as to adjust the signal power of the microwave signal, thereby finally realizing the distribution of the microwave signals to the n accelerating tubes according to the target microwave power distribution ratio.

In the embodiments of the present disclosure, optionally, the microwave transmission sub-module may be a circulator with m ports, wherein m is an integer greater than n. That is, m is an integer greater than or equal to n+1.

The $1^{st}$ port of the circulator is connected to the microwave signal generation module, and the $2^{nd}$ port to the $(n+1)^{th}$ port of the circulator are connected to the n power regulation sub-modules, respectively. That is, each of the $2^{nd}$ to $(n+1)^{th}$ ports is connected to one power regulation sub-module. For example, when n is 5, each of the $2^{nd}$ to $6^{th}$ ports of the circulator is connected to one power regulation sub-module.

Optionally, n may be 2, and m may be 4. When m is 4, the microwave transmission sub-module is a circulator with four ports, namely, a four-port circulator. For example, the two power regulation sub-modules include a first power regulation sub-module and a second power regulation sub-module; and the two accelerating tubes include a first accelerating tube and a second accelerating tube. When the microwave transmission sub-module is a four-port circulator, the first port of the four-port circulator is connected to the microwave signal generation module, the second port of the four-port circulator is connected to the first power regulation sub-module, the third port of the four-port circulator is connected to the second power regulation sub-module, and the fourth port of the four-port circulator may be configured to be connected to a microwave load. The microwave load is configured to absorb the microwave signal input from the fourth port.

Figure 5:
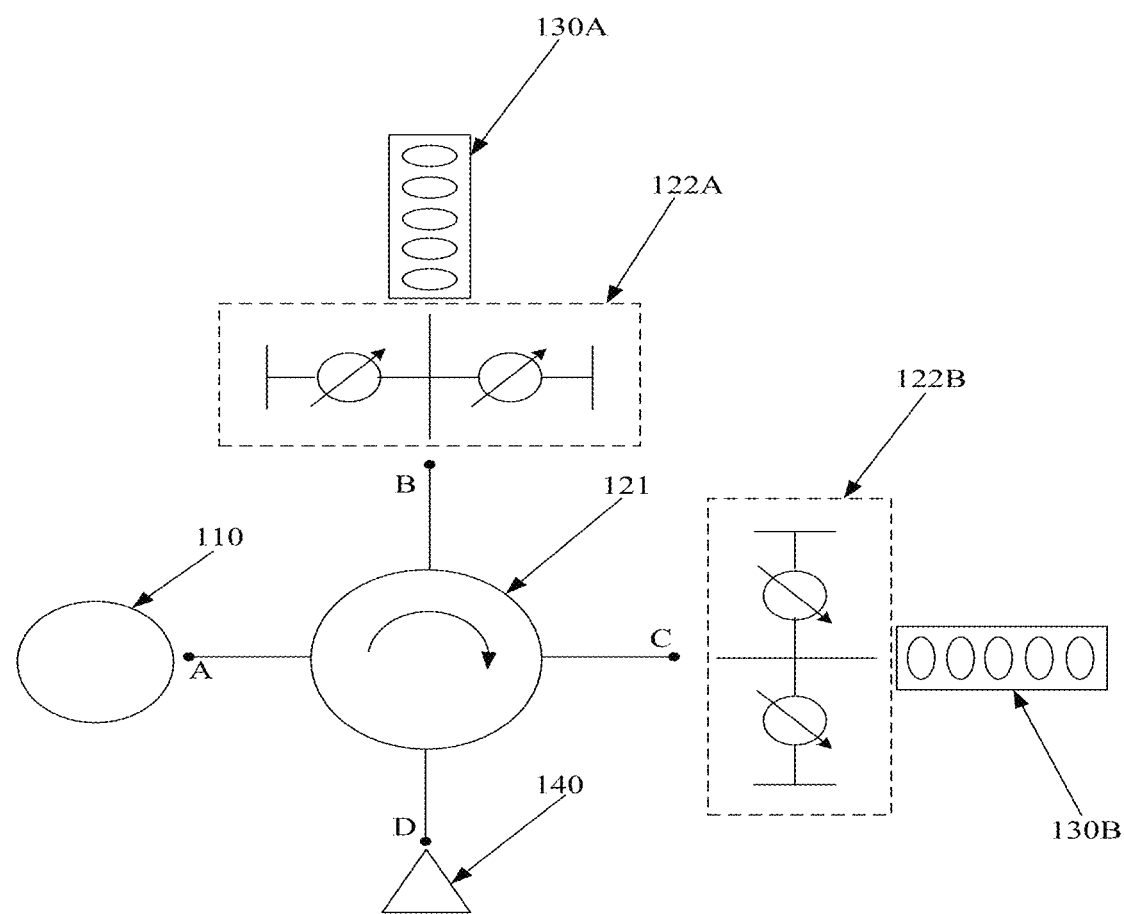
FIG. 5 is a schematic diagram showing an application scenario of yet another microwave power control device according to an embodiment of the present disclosure.

FIG. 5 is a schematic diagram showing an application scenario of yet another microwave power control device according to an embodiment of the present disclosure. The microwave transmission sub-module in the microwave power control device is a four-port circulator. As shown in FIG. 5, the first port A of the four-port circulator 121 is connected to the microwave signal generation module 110 via a transmission waveguide, and is configured to transmit the microwave signal generated by the microwave signal generation module 110 to the second port B of the four-port circulator 121.

The second port B of the four-port circulator 121 is connected to the input end of the first power regulation sub-module 122A by a transmission waveguide, and the output end of the first power regulation sub-module 122A is connected to the first accelerating tube 130A. The first power regulation sub-module 122A is configured to distribute the microwave signal input to the second port B of the four-port circulator to the first accelerating tube 130A according to the target microwave power distribution ratio, and output the microwave signal of the residual power to the third port C of the four-port circulator 121 through the second port B of the four-port circulator 121.

The third port C of the four-port circulator 121 is connected to the input end of the second power regulation sub-module 122B via a transmission waveguide, and the output end of the second power regulation sub-module 122B is connected to the second accelerating tube 130B. The second power regulation sub-module 122B distributes the microwave signal input to the third port C of the four-port circulator to the second accelerating tube 130B according to the target microwave power distribution ratio, and output the microwave signal of the residual power to the fourth port D of the four-port circulator 121 through the third port C of the four-port circulator 121.

The fourth port D of the four-port circulator 121 is configured to be connected to the microwave load 140; and the microwave load 140 is configured to absorb the microwave signal input to the fourth port D of the four-port circulator 121.

In summary, the microwave power control device provided by the embodiment of the present disclosure includes the microwave signal generation module and the distribution module, wherein the microwave signal generation module generates the microwave signals and transmits the microwave signals to the distribution module, and the distribution module distributes the microwave signals to at least two accelerating tubes according to the target microwave power distribution ratio. Compared with related arts, as one microwave power control device can drive at least two accelerating tubes at a time, the microwave power control device is richer in function, and the cost of the radiotherapy equipment can be reduced.

Figure 6:
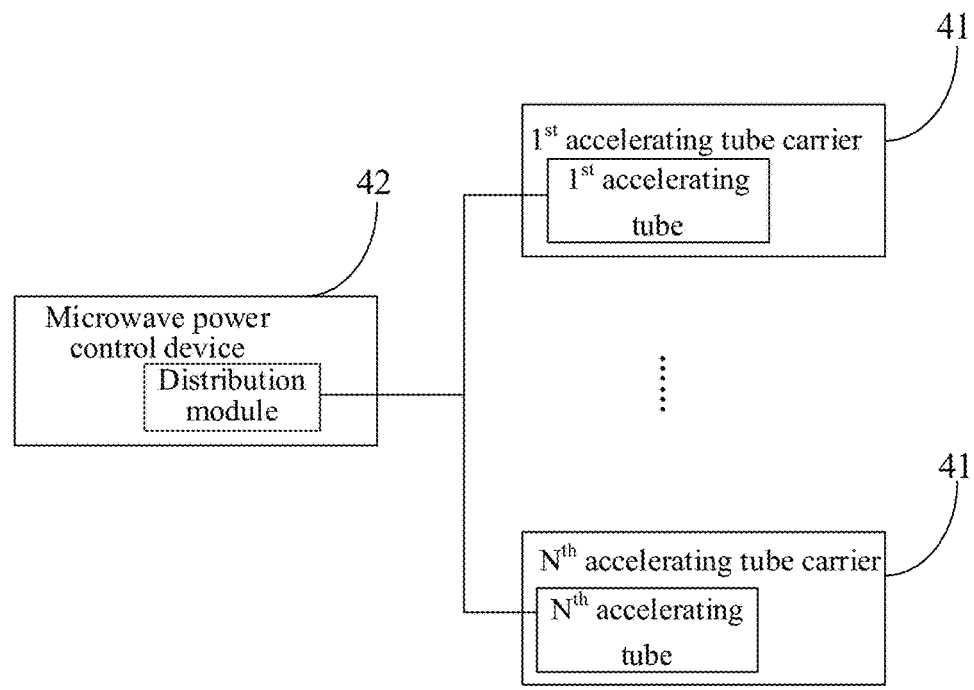
FIG. 6 is a schematic structural diagram of a radiotherapy equipment according to an embodiment of the present disclosure.

FIG. 6 is a schematic structural diagram of a radiotherapy equipment according to an embodiment of the present disclosure. As shown in FIG. 6, the radiotherapy equipment includes: n accelerating tube carriers 41, and a microwave power control device 42 which may be the microwave power control device as shown in FIG. 1, FIG. 2, FIG. 3 or FIG. 5.

An accelerating tube in each of the accelerating tube carriers 41 is connected to a distribution module of the microwave power control device 42.

Optionally, the accelerating tube carrier includes at least one of an X-ray treatment head and an X-ray diagnostic head. That is, the accelerating tube carrier includes the X-ray treatment head, or includes the X-ray diagnostic head, or includes both the X-ray treatment head and the X-ray diagnostic head. The embodiment of the present disclosure does not limit the type of the accelerating tube carrier.

The X-ray treatment head is configured to emit a treatment beam (for example, an MV-level X-ray) to treat an affected part of a patient. The X-ray diagnostic head is configured to emit an imaging beam (for example, a KV-level X-ray) for imaging diagnosis of the patient. An energy level of the imaging beam may be different from that of the treatment beam.

Figure 7:
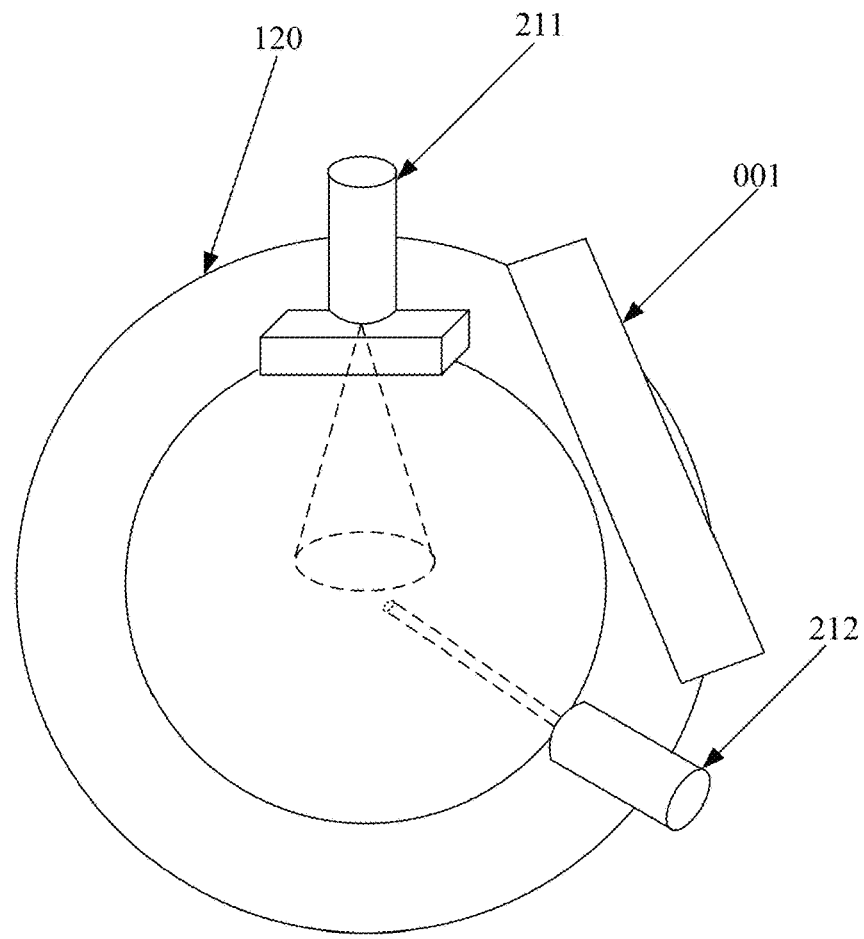
FIG. 7 is a schematic diagram of an X-ray treatment head arranged on a gantry according to an embodiment of the present disclosure.

Optionally, FIG. 7 is a schematic diagram of an X-ray treatment head arranged on a gantry according to an embodiment of the present disclosure. As shown in FIG. 7, when n is 2, each of the X-ray treatment head may include an X-ray conformal intensity modulation treatment head and an X-knife treatment head. That is, the radiotherapy equipment includes: the X-ray conformal intensity modulation treatment head, the X-knife treatment head, and the microwave power control device for outputting the microwave signals to the accelerating tubes of the two X-ray treatment heads to drive the two accelerating tubes. The X-ray conformal intensity modulation treatment head includes an accelerator with an accelerating tube and a multi-leaf collimator. The multi-leaf collimator is configured to perform conforming on the X-ray emitted by the accelerator. The X-knife treatment head includes an accelerator with an accelerating tube and a collimator. The collimator may be a collimator with multiple beam channels of different aperture sizes, or may be a collimator with a single beam channel having an adjustable shape and/or size.

Certainly, when n is 2, the X-ray treatment heads may be both X-ray conformal intensity modulation treatment heads, or both X-knife treatment heads.

Further, the radiotherapy equipment further includes a gantry, and the n accelerating tube carriers and the microwave power control device are all arranged on the gantry. The gantry may be a rotating gantry, and the n accelerating tube carriers and the microwave power control device can rotate in a reciprocating way or rotate by 360° continuously around a rotating shaft of the rotating gantry.

In the embodiment of the present disclosure, the X-ray treatment head can move or swing axially along the rotating shaft of the rotating gantry, so as to realize non-coplanar treatment of the patient. For example, an arc-shaped guide rail can be arranged on the rotating gantry, and the X-ray treatment head is arranged on the arc-shaped guide rail, and can move or swing axially along the rotating shaft of the rotating gantry on the arc-shaped guide rail. In another example, a pivot shaft may be arranged on the rotating gantry, the X-ray treatment head is connected to the pivot shaft, and can pivot or swing axially around the pivot shaft along the rotating shaft of the rotating gantry.

In example embodiments, continuing to refer to FIG. 7, the X-ray treatment head 211 can rotate along with the rotation of the rotating gantry 120, and the X-ray treatment head 212 can swing axially along the rotating shaft of the rotating gantry 120, so as to realize the non-coplanar treatment of the patient. The accelerating tubes in the two X-ray treatment heads are driven by the same microwave power control device 001.

Figure 8:
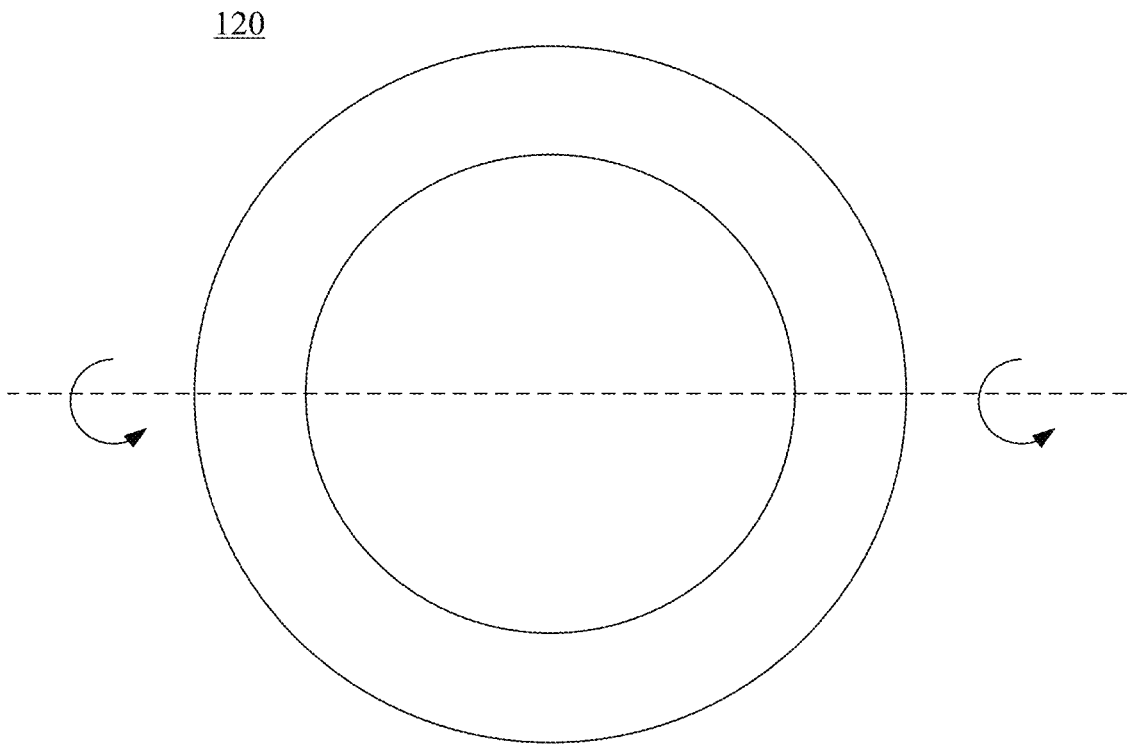
FIG. 8 is a schematic diagram showing the gantry swinging with a horizontal diameter as an axis according to an embodiment of the present disclosure.

In addition, the rotating gantry 120 may also swing with the radial direction as an axis, and the X-ray treatment head can move or swing axially along the rotating shaft of the rotating gantry as the rotating gantry swings, so as to realize the non-coplanar treatment of the patient. In example embodiments, as shown in FIG. 8, the rotating gantry 120 can swing with a horizontal diameter as the axis, and the X-ray treatment head can swing axially along the rotating shaft of the rotating gantry as the rotating gantry 120 swings, so as to realize the non-coplanar treatment of the patient.

Further, the radiotherapy equipment may further include a treatment couch, wherein the treatment couch is configured to carry the patient so that the patient can move along with the movement of the treatment couch.

It should be noted that, in the embodiment of the present disclosure, a drum-type gantry is taken as an example of the gantry. In example embodiments, the gantry may also be in a shape of a C-shaped arm, a cantilever, a semiarc, or the like.

In summary, in the radiotherapy equipment provided by the embodiment of the present disclosure, the microwave power control device in the radiotherapy equipment includes the microwave signal generation module and the distribution module. The microwave signal generation module generates the microwave signals and transmits the microwave signals to the distribution module, and the distribution module distributes the microwave signals to at least two accelerating tubes according to the target microwave power distribution ratio. Compared with related arts, as one microwave power control device can drive at least two accelerating tubes at a time, a plurality of the accelerating tubes can be provided with only one microwave power control device. Therefore, the volume of the radiotherapy equipment can be reduced, thereby reducing the manufacturing, maintenance and overhaul costs.

Figure 9:
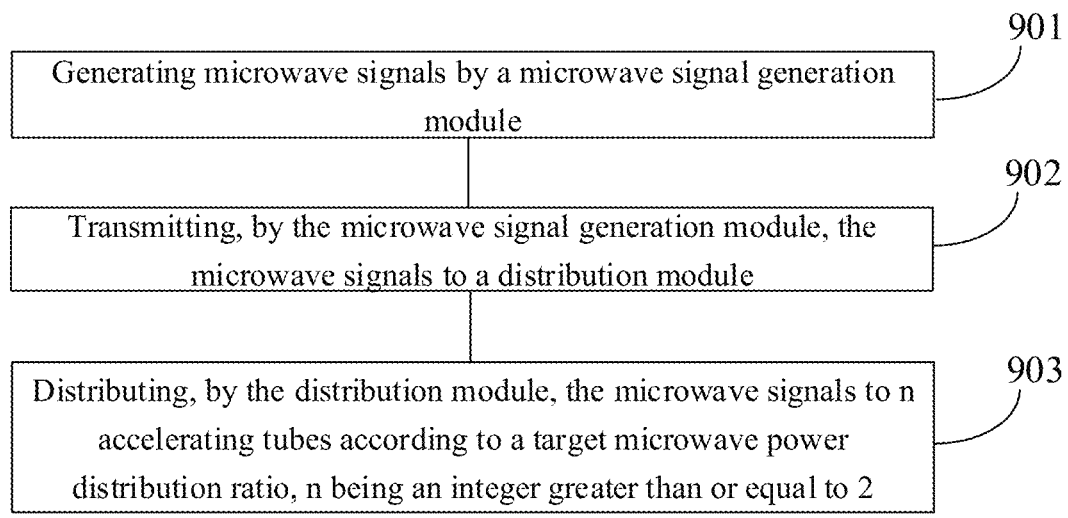
FIG. 9 is a flowchart showing a microwave power control method according to an embodiment of the present disclosure.

FIG. 9 is a flowchart showing a microwave power control method according to an embodiment of the present disclosure. The method is applicable to the microwave power control device provided in any one of the above embodiments. As shown in FIG. 9, the method includes the following working processes.

In step 901, a microwave signal generation module generates microwave signals.

In step 902, the microwave signal generation module transmits the microwave signals to a distribution module.

In step 903, the distribution module distributes the microwave signals to n accelerating tubes according to a target microwave power distribution ratio, wherein n is an integer greater than or equal to 2.

In summary, in the microwave power control method provided by the embodiment of the present disclosure, the distribution module of the microwave power control device can distribute the microwave signals to at least two accelerating tubes according to the target microwave power distribution ratio. Compared with related arts, as one microwave power control device can drive at least two accelerating tubes at a time, the functions are richer, and the cost is reduced.

Figure 10:
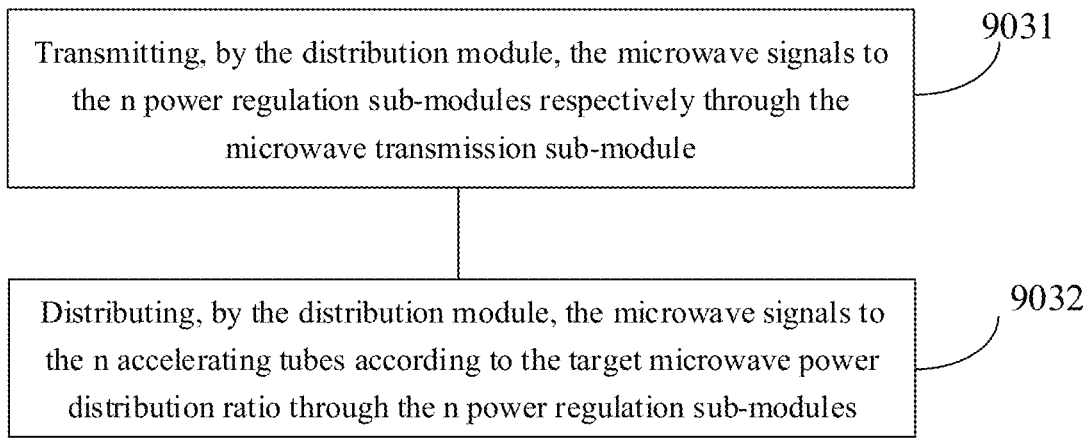
FIG. 10 is a flowchart showing a distribution module distributing microwave signals to accelerating tubes according to an embodiment of the present disclosure.

As shown in FIG. 3, the distribution module 120 may include: a microwave transmission sub-module 121 and n power regulation sub-modules 122. As shown in FIG. 10, the above step 903 may include the following steps.

In step 9031, the microwave transmission sub-module transmits the microwave signals generated by the microwave signal generation module to the n power regulation sub-modules respectively.

In step 9032, the n power regulation sub-modules respectively distributes the microwave signals to the n accelerating tubes according to the target microwave power distribution ratio.

It should also be noted that the steps of the microwave power control method provided by the embodiment may be correspondingly increased or omitted as needed. Modified methods which can be easily conceived by those persons skilled in the art within the technical scope disclosed by the present disclosure should be encompassed by the protection scope of the present disclosure.

Those persons skilled in the art can clearly understand that for the sake of convenient and brief description, for particular working processes of the above steps, reference can be made to the particular working processes of the corresponding modules and sub-modules in the foregoing device embodiments, and details are not repeated herein.

In summary, in the microwave power control method provided by the embodiment of the present disclosure, the distribution module of the microwave power control device can distribute the microwave signals to at least two accelerating tubes according to the target microwave power distribution ratio. Compared with related arts, as one microwave power control device can drive at least two accelerating tubes at a time, the functions of the microwave power control device are richer, and the cost is reduced.

Figure 11:
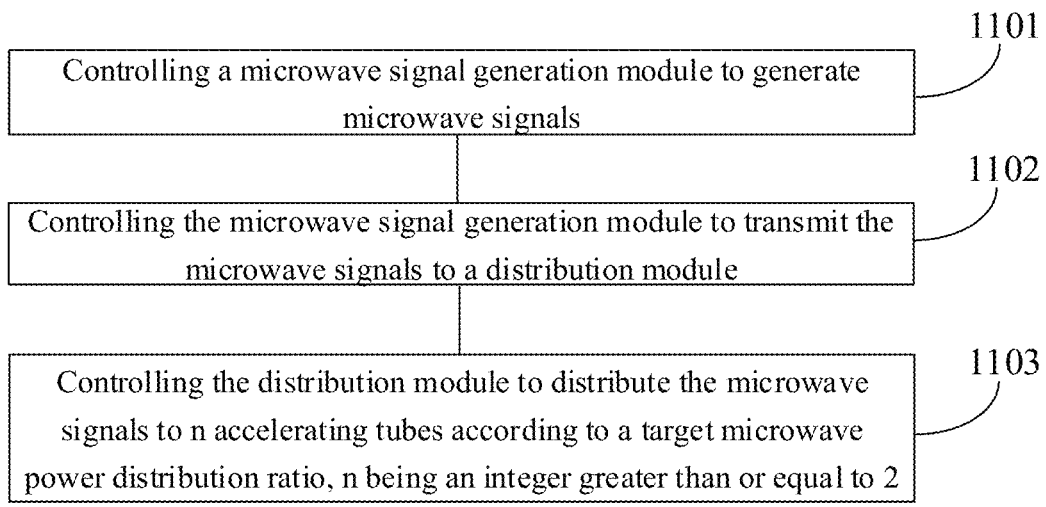
FIG. 11 is a flowchart showing another microwave power control method according to an embodiment of the present disclosure.

FIG. 11 is a flowchart showing another microwave power control method according to an embodiment of the present disclosure. The method is applicable to the radiotherapy equipment provided in any one of the above embodiments. As shown in FIG. 11, the method includes the following working processes.

In step 1101, a microwave signal generation module is controlled to generate microwave signals.

In step 1102, the microwave signal generation module is controlled to transmit the microwave signals to a distribution module.

In step 1103, the distribution module is controlled to distribute the microwave signals to n accelerating tubes according to a target microwave power distribution ratio, wherein n is an integer greater than or equal to 2.

Further, the distribution module 120 may include: a microwave transmission sub-module 121 and n power regulation sub-modules 122. The above step 1103 may include the following steps.

In step S31, the microwave transmission sub-module is controlled to transmit the microwave signals generated by the microwave signal generation module to the n power regulation sub-modules, respectively.

In step S32, the n power regulation sub-modules are controlled to distribute the microwave signals to the n accelerating tubes according to the target microwave power distribution ratio.

Some embodiments of the present disclosure further provide a computer-readable storage medium which is a nonvolatile readable storage medium, wherein the computer-readable storage medium stores instructions; and when run on a processing component, the readable storage medium causes the processing component to execute the microwave power control methods applied to the radiotherapy equipment.

Some embodiments of the present disclosure further provide a microwave power control device, including a memory, a processor, and a computer program stored in the memory and capable of running on the processor, wherein the computer program, when executed by the processor, performs the microwave power control method applicable to the radiotherapy equipment.

The embodiments of the present disclosure further provide a computer program product containing instructions stored in the computer program product; and when run on a computer, the instructions cause the computer to execute the microwave power control methods applicable to the radiotherapy equipment.

Some embodiments of the present disclosure further provide a chip, including programmable logic circuits and/or program instructions, wherein when the chip is run, the chip executes the microwave power control methods applicable to the radiotherapy equipment.

It may be understood by an ordinary person skilled in the art that all or part of steps in the above embodiments can be completed by hardware or by a program to instruct relevant hardware to implement the steps. The program can be stored in a computer-readable storage medium such as an ROM, a magnetic disk, an optical disc or the like.

The foregoing descriptions are only optional embodiments of the present disclosure, and are not intended to limit the present disclosure. Any modification, equivalent substitution, improvement and the like that fall within the concept and principle of the present disclosure should be embraced by the protective scope of the present disclosure.

What is claimed is:

1. A microwave power control device, comprising: a microwave signal generator and a signal distribution circuitry connected to the microwave signal generator, wherein
the microwave signal generator is configured to generate microwave signals and transmit the microwave signals to the signal distribution circuitry; and
the signal distribution circuitry is configured to distribute the microwave signals to n accelerating tubes according to a target microwave power distribution ratio, n being an integer greater than or equal to 2,
wherein the signal distribution circuitry comprises: a microwave transmission circuitry and n power regulation circuitries,
wherein the microwave transmission circuitry is connected to the microwave signal generator, and is configured to respectively transmit the microwave signals generated by the microwave signal generator to the n power regulation circuitries; and the n power regulation circuitries are configured to distribute the microwave signals to the n accelerating tubes according to the target microwave power distribution ratio,
wherein each of the n power regulation circuitries is an adjustable power switch comprising: a coupler, a first adjustable phase shifter, and a second adjustable phase shifter, and
wherein a first end of the coupler is connected to the microwave transmission circuitry, a second end of the coupler is connected to a first short-circuit waveguide via the first adjustable phase shifter, a third end of the coupler is connected to a second short-circuit waveguide via the second adjustable phase shifter, and a fourth end of the coupler is connected to a corresponding accelerating tube.

2. The device according to claim 1, wherein the microwave transmission circuitry is a circulator with m ports, m being an integer greater than or equal to n+1; and
wherein a first port of the circulator is connected to the microwave signal generator, and a second port to a $(n+1)^{th}$ port of the circulator are respectively connected to the n power regulation circuitries.

3. The device according to claim 2, wherein n is 2, m is 4, and a $4^{th}$ port of the circulator is connected to a microwave load.

4. The device according to claim 1, wherein the microwave signal generator comprises a solid-state modulator and a magnetron.

5. A microwave power control method, applicable to the microwave power control device of claim 1, the method comprising:
generating microwave signals by the microwave signal generator of claim 1;
transmitting, by the microwave signal generator, the microwave signals to the signal distribution circuitry of claim 1; and
distributing, by the signal distribution circuitry, the microwave signals to the n accelerating tubes of claim 1 according to the target microwave power distribution ratio, n being an integer greater than or equal to 2.

6. A microwave power control device, comprising: a memory and a processor, wherein:
a computer program is stored in the memory; and
the computer program, when executed by the processor, causes the processor to perform the microwave power control method of claim 5.

7. A non-transitory computer-readable storage medium storing instructions thereon, wherein the instructions, when executed by a processor, cause the processor to perform the microwave power control method of claim 5.

8. A radiotherapy equipment, comprising: n accelerating tube carriers and a microwave power control device, wherein the microwave power control device comprises:
a microwave signal generator and a signal distribution circuitry connected to the microwave signal generator;
the microwave signal generator is configured to generate microwave signals and transmit the microwave signals to the signal distribution circuitry; and the signal distribution circuitry is configured to distribute the microwave signals to n accelerating tubes according to a target microwave power distribution ratio, n being an integer greater than or equal to 2; and wherein an accelerating tube in each of the n accelerating tube carriers is connected to the signal distribution circuitry of the microwave power control device, wherein the signal distribution circuitry comprises: a microwave transmission circuitry and n power regulation circuitries, wherein the microwave transmission circuitry is connected to the microwave signal generator, and is configured to respectively transmit the microwave signals generated by the microwave signal generator to the n power regulation circuitries; and the n power regulation circuitries are configured to distribute the microwave signals to the n accelerating tubes according to the target microwave power distribution ratio, wherein each of the n power regulation circuitries is an adjustable power switch comprising:

a coupler, a first adjustable phase shifter, and a second adjustable phase shifter, and wherein a first end of the coupler is connected to the microwave transmission circuitry, a second end of the coupler is connected to a first short-circuit waveguide via the first adjustable phase shifter, a third end of the coupler is connected to a second short-circuit waveguide via the second adjustable phase shifter, and a fourth end of the coupler is connected to a corresponding accelerating tube.

9. The equipment according to claim 8, wherein each of the n accelerating tube carriers comprises: at least one of an X-ray treatment head or an X-ray diagnostic head.

10. The equipment according to claim 9, wherein when n is 2, the X-ray treatment head comprises an X-ray conformal intensity modulation treatment head and an X-knife treatment head.

11. The equipment according to claim 8, further comprising a gantry, wherein the n accelerating tube carriers and the microwave power control device are arranged on the gantry.

12. A microwave power control method, applicable to the radiotherapy equipment of claim 8, the method comprising:
controlling the microwave signal generator of claim 8 to generate microwave signals;
controlling the microwave signal generator to transmit the microwave signals to the signal distribution circuitry of claim 8; and
controlling the signal distribution circuitry to distribute the microwave signals to the n accelerating tubes of claim 8 according to the target microwave power distribution ratio, n being an integer greater than or equal to 2.

13. A microwave power control device, comprising: a memory and a processor, wherein:
a computer program is stored in the memory; and
the computer program, when executed by the processor, causes the processor to perform the microwave power control method of claim 12.

14. A non-transitory computer-readable storage medium storing instructions thereon, wherein the instructions, when executed by a processor, cause the processor to perform the microwave power control method of claim 12.

* * * * *